United States Patent [19]

Curtiss

[11] Patent Number: 5,778,887
[45] Date of Patent: Jul. 14, 1998

[54] FACE DOWN BODY SUPPORT APPARATUS

[76] Inventor: Frederic M. Curtiss. 360 Coral Dr., SW, Fort Walton Beach, Fla. 32548

[21] Appl. No.: 603,364

[22] Filed: Feb. 20, 1996

Related U.S. Application Data

[63] Continuation-in-part of Ser. No. 494,191, Jun. 23, 1995, abandoned.

[51] Int. Cl.⁶ ............................................. A61G 15/00
[52] U.S. Cl. .............................. 128/845; 5/637; 5/638
[58] Field of Search ..................... 128/845, 846; 602/5, 35, 36; 5/461, 632, 638, 625, 636, 637

[56] References Cited

U.S. PATENT DOCUMENTS

| | | | |
|---|---|---|---|
| 2,389,269 | 11/1945 | Mermis | 5/637 |
| 2,795,802 | 6/1957 | Myers | 5/337 |
| 2,803,022 | 8/1957 | Wynkoop | 5/327 |
| 3,009,172 | 11/1961 | Eidam | 5/338 |
| 3,114,527 | 12/1963 | Demarest | 248/118 |
| 3,140,497 | 7/1964 | Carswell | |
| 4,193,150 | 3/1980 | Vineberg | 5/431 |
| 4,320,543 | 3/1982 | Dixon | 5/637 |
| 4,823,776 | 4/1989 | Foster | 5/638 |
| 5,095,569 | 3/1992 | Glenn | 5/490 |
| 5,177,823 | 1/1993 | Riach | 5/636 |
| 5,224,226 | 7/1993 | Groenwald | 5/481 |
| 5,337,760 | 8/1994 | Nichols | 128/845 |
| 5,520,623 | 5/1996 | Williams | 5/637 |

*Primary Examiner*—Michael A. Brown
*Attorney, Agent, or Firm*—Troutman Sanders LLP; Joel S. Goldman; Gerald R. Boss

[57] ABSTRACT

The apparatus of the present invention includes a rigid member for supporting a person's body, two rigid extensions which extend outwardly from the rigid member and a forehead support member which is coupled to the two extensions. The rigid member preferably includes a contoured padding to comfortably support the person's abdomen, chest and neck areas, and a recessed padded portion to support a person's chin. The forehead support member is preferably formed of a flexible strap or rigid pad and is longitudinally adjustable along the length of the rigid extensions. The apparatus is positioned on a bed such that the rigid extensions are cantilevered from the head of the bed. The person then rests his or her abdomen, chest, and neck onto the contoured padding of the rigid member, chin into the padded recessed portion and forehead onto the forehead support member.

18 Claims, 5 Drawing Sheets

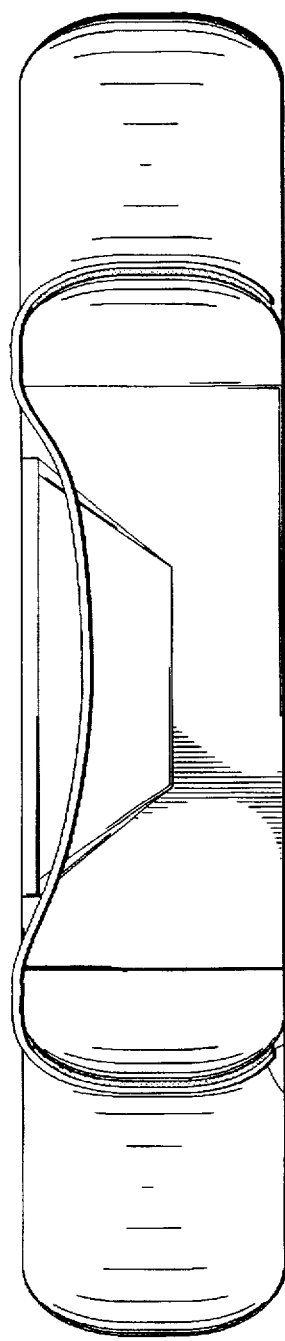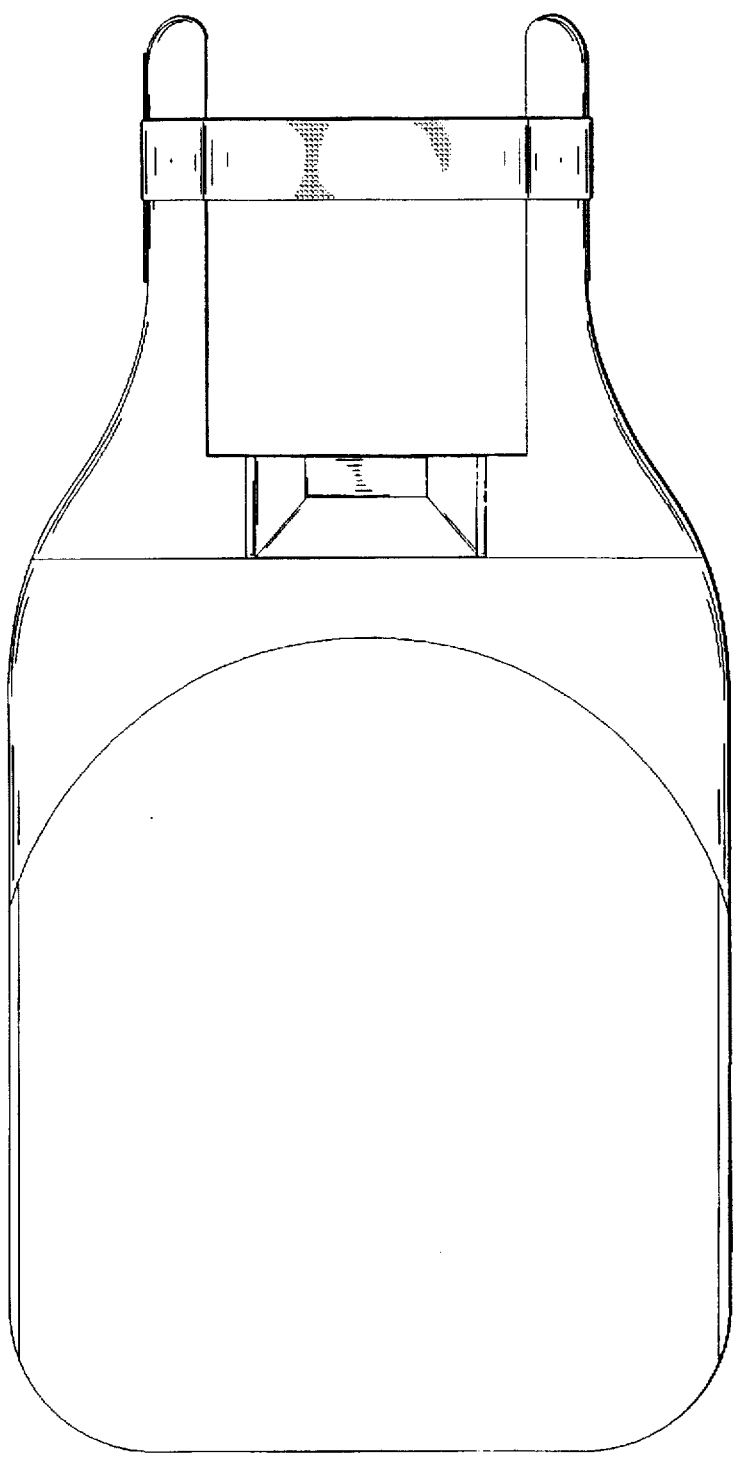
FIG. 2
FIG. 3

FACE DOWN BODY SUPPORT APPARATUS

This application is a Continuation-in-Part of parent application Ser. No. 08/494,191, filed on Jun. 23, 1995, now abandoned.

BACKGROUND OF THE INVENTION

1. Technical Field

This invention relates generally to an apparatus for supporting a person's body in the face down position. More specifically, the present invention relates to an apparatus for supporting a person who is required to lie face-down for an extended period of time.

2. Description of the Prior Art

In the past, apparatuses for supporting a person's body in the face down position have been used for a variety of purposes. However, most often such apparatuses have been used in the medical profession for patients who are required to lay face down during post operative medical procedures. For example, after many types of eye operations, such as that for a ruptured retina, a face down apparatus is often used after the operation to allow the eye to heal properly.

U.S. Pat. No. 5,095,569 discloses a face down body support apparatus in the form of a wedge shaped pillow which may be rested on a bed. The wedge shaped pillow includes an air passageway leading to opposed transverse vent passages which allow a patient to breath while laying face down. However, as disclosed, this apparatus does not provide a contoured surface for the patient's body. Also, this apparatus does not include a rapid upper portion such that the upper portion may be cantilevered from the head of a bed. Further, this apparatus does not allow the patient to see downward below the apparatus but rather forces the patient to look into a black hole. As a result, the patient is prevented from reading, watching television and the like during recovery.

Another alternative for supporting a patient's body in the face down position is seemingly more primitive but is nonetheless currently used by many doctors. This alternative is typically used in a recovery room at a hospital, and utilizes a bed (i.e., a medical bed) and a table (i.e., a serving table) adjusted to the same height as the bed. The table is typically positioned against a wall and the head of the bed, is positioned approximately one foot from the table. A pillow is placed on the table, and any headboard on the bed is removed. The patient then rests his or her body from approximately the chest down on the bed and rests his or her forehead on the pillow. As is readily apparent, this alternative is lacking in comfort, precision, and simplicity due to the variety of beds, tables an the like that are found in different hospital rooms. Further, this alternative does not provide any means for keeping the patient's head in a stable position.

The above-described disadvantages of the prior art apparatuses for supporting a person's body in the face down position are effectively overcome by the present invention, as described in further detail below.

SUMMARY OF THE INVENTION

In accordance with the teachings of the present invention, a new apparatus for supporting a person's body in the face down position is provided. The present invention is particularly useful as an accessory in medical procedures.

The present invention introduces an apparatus for supporting a person's body in the face down position, which provides more comfort, precision, stability and simplicity than similar prior art apparatuses. The present invention also provides a rigid upper portion of the apparatus which may be cantilevered from the bed, provides an opening for the person to see below the apparatus, provides a means for sustaining the person in a face down position and provides much more.

In a preferred embodiment, the apparatus of the present invention includes a rigid member for supporting a person's body, two rigid extensions which extend outwardly from the rigid member and a forehead support member which is coupled to the two extensions. The rigid member may be constructed of a rigid, light-weight, high-strength, and biodegradable plastic material. The rigid member may be injection- or blow-molded by standard plastic forming equipment. Such a light-weight, rigid member provides the advantage of easy transport by hospital personnel or patients, while allowing the apparatus to be discarded in its entirety after use due to the biodegradable nature of its rigid plastic material.

A top surface of the rigid member preferably includes a contoured padding surface with a curvature conforming substantially to the shape of a portion of a person's abdomen, neck and chest areas, thereby comfortably supporting the person's abdomen, chest and neck areas, and a recessed padded portion to support a person's chin. In a preferred embodiment, the contour padding may include a soft, pliable polymeric foam having an "egg-shell" or "egg-carton" surface contour, which provides maximum comfort for the person using the apparatus. The soft, pliable polymeric foam padding may also be biodegradable, thus allowing the entire apparatus to be discarded in landfills without significant environmental impact.

The forehead support member is preferably formed of a flexible strap or rigid pad extending between the rigid extensions. The forehead support member may also be longitudinally adjustable along the length of the rigid extensions to accommodate patients of varying heights and neck length. Although virtually any material may comprise a flexible strap strung between the rigid extensions, in a preferred embodiment, the forehead support member may be comprised of a flexible nylon strap including hook and loop fasteners on ends of the strap. Additionally, each rigid extension may include a hook and loop fasteners section on an outer portion thereof to accept complimentary portions on the strap, thereby allowing the strap to securely drape between the rigid extensions in a manner which adequately and comfortably supports the patient's head.

Additionally, a preferred embodiment includes padding on the flexible head supporting strap. Although virtually any padding may be utilized, in a preferred embodiment, the nylon strap may include an "egg-shell"-type foam padding removably attached by hook and loop fasteners to a top side of the head supporting strap for providing further comfort to the head of a person utilizing the face-down apparatus.

Finally, the preferred embodiment of the present invention may also include an over-head strap for securing the person's head firmly into the head supporting strap. The over-head strap may include means for attaching it to the extensions, and means for providing further comfort to the patient. For example, although a multitude of materials may be used for padding, the over-head strap may include a nylon strap having hook and loop fastener strips on its end portions for attaching the strap to the hook and loop fastener strips on the outer portions of the apparatus extensions. The over-head strap may also include foam padding on inside portions thereof for centering the patient's head and for providing patient comfort. In a preferred embodiment, the overhead strap may include triangular pads removably attached its bottom surface for engaging side portions of the patient's head, thereby centering the patient's head between the rigid extensions and securing the patient's head against the head supporting strap. The over-head strap padding may also include polymeric foam padding having the "egg-carton"-type surface contour.

The preferred embodiment of the face-down apparatus may also include means on the head supporting strap for attaching the overhead strap to the rigid extensions. For example, rather than fastening the overhead strap directly to the rigid extensions, outside ends of the overhead strap may also include hook and loop fastener strips for mating with the hook and loop fastener strips on the overhead strap, thus allowing the overhead strap to be fastened either to the outside ends of the head supporting strap, or directly to outer portions of the rigid extension.

The apparatus is positioned on a bed such that the rigid extensions are cantilevered from the head of the bed. The person then rests his or her abdomen, chest, and neck onto the contoured padding of the rigid member. The person may then rest his or her chin into the padded recessed portion and forehead onto the forehead support member. As described above, the forehead support member is easily adjustable along the longitudinal axis of the rigid extensions so that the forehead support member may be adjustably positioned for a comfortable and snug fit.

By resting a majority of the person's body weight on the rigid member of the apparatus, the person's body acts as the stabilizing means for keeping the apparatus in place on the bed. Therefore, the apparatus need not be fastened down to the bed.

Further, by cantilevering the person's head over the head of the bed and providing the opening between the recessed chin portion and the adjustable forehead support member, the person is provided with ample breathing space. Further, this opening allows the person to see below the apparatus for reading, viewing of television and the like.

Moreover, the contoured padding on the rigid member, the recessed chin portion and the adjustable forehead support member provide a means for sustaining the person in the face down position. This aspect of the invention is of particular importance for a medical patient, such as a postoperative patient recovering from an eye operation, who is required to lay face down for an extended period of time.

BRIEF DESCRIPTION OF THE DRAWINGS

The accompanying drawings illustrate several presently preferred, but nevertheless illustrative, embodiments of the present invention and serve to aid in the explanation of the principles of the invention.

FIG. 2 is a lateral cross-sectional view of the face down body support apparatus of the present invention using hook and loop fastener on the rigid extensions and forehead support member.

FIG. 3 is a perspective view from above of the face down body support apparatus of the present invention using hook and loop fastener on the rigid extensions and forehead support member.

DETAILED DESCRIPTION OF THE PREFERRED EMBODIMENT

Figure 1:
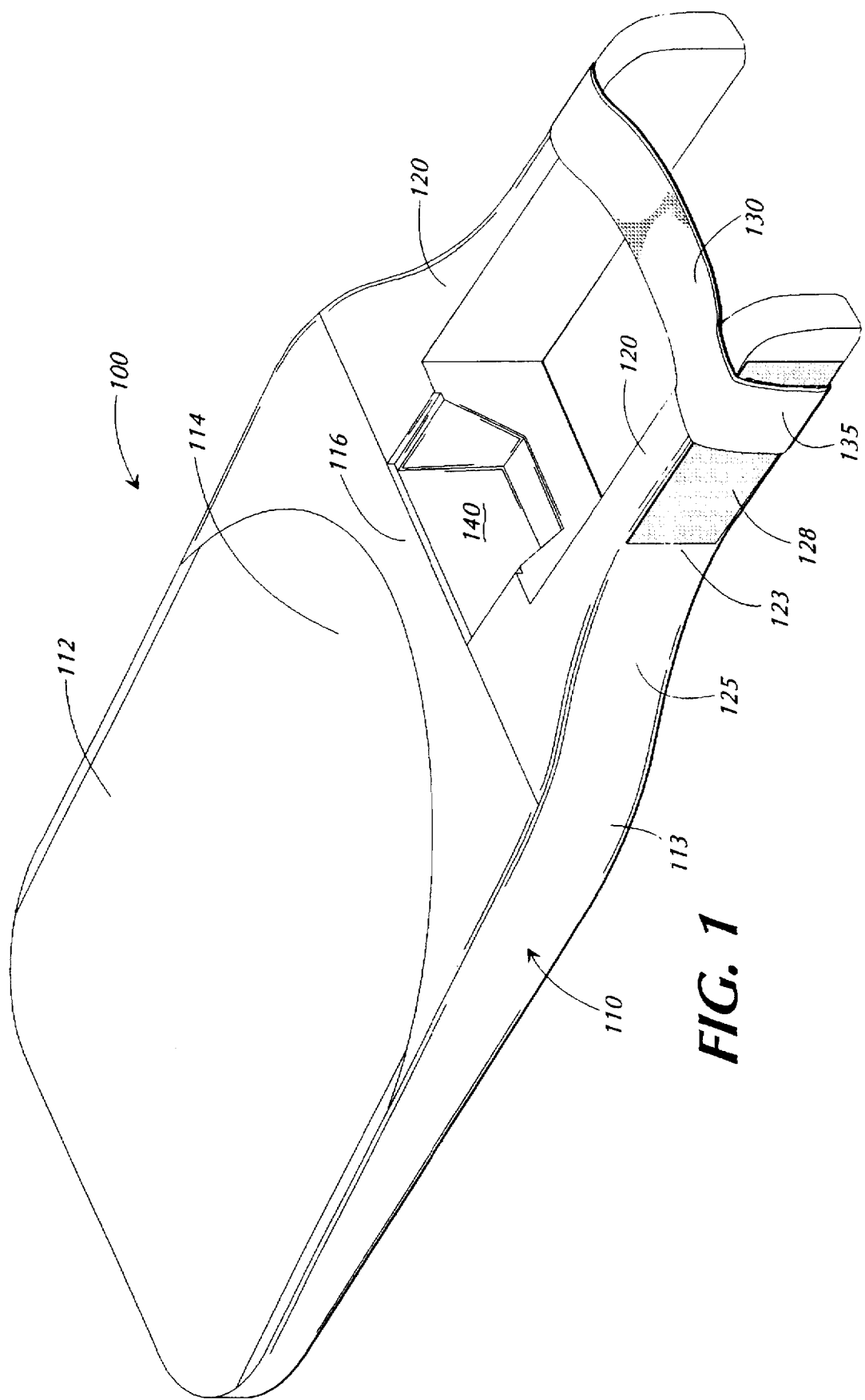
FIG. 1 is a perspective view of the face down body support apparatus of the present invention using hook and loop fasteners on the rigid extensions and forehead support member.

FIGS. 1 to 3 illustrate the face down body support apparatus 100 according to the present invention. The apparatus 100 includes a rigid member 110 for supporting a person's body, two rigid extensions 120 which extend outwardly from a forward portion 113 of the rigid member 110 and a forehead support member 130 coupled to the two rigid extensions 120.

The rigid member 110 has a top surface gradually increasing in height approaching the forward portion and preferably includes a contoured abdomen padding 112, chest padding 114 and neck padding 116 to comfortably support these respective portions of a person's body. A recessed member 140, which is preferably padded, extends downwardly from the upper portion 113 of the rigid member 110 to comfortably accept and support a person's chin.

The rigid member 110, including the recessed member 140, are preferably formed of a sufficiently stiff, lightweight, biodegradable plastic. Biodegradable plastic material is defined herein as plastic which readily breaks down into nontoxic components. Examples of mechanisms by which a plastic material may be biodegraded include, but are not limited to, hydrolysis, oxidation, ultraviolet light exposure, or enzymatic exposure. Examples of such plastics may be, but are not limited to polyethylene (including but not limited to ultrahigh molecular weight polyethylene), polyethylene terepthalate, polypropylene, or other plastic material having additives which facilitate biodegradation.

Padding for the abdomen padding 112, chest padding 114 and neck padding 116 is preferably formed of an "egg carton" type of foam covered with a stain resistant material. All padding is preferably formed from a biodegradable polymer foam. Such a foam may be formed from urethane, for example, with additives for allowing the foam to readily break down after the apparatus is discarded in a land fill. Further, the recessed member 140 is preferably formed of a soft foam covered with a stain resistant material.

The outer portions 123 of the rigid extensions 120 preferably taper inward slightly as these extensions 120 extend away from the upper portion 113 of the rigid member 110 to approximately the mid-portion of each rigid extension 120. At the mid-portion, each rigid extension 120 substantially straightens out such that the outer portion 123 of the rigid extensions 120 are substantially parallel.

The tapered portion of the rigid extensions 120 provides an arm rest 125 for a person to comfortably support his or her arms. The outer portion 123 of each rigid extension 120 which is substantially parallel preferably includes a hook and loop fastener strip 128 extending substantially longitudinally along the length of the outer portion 123 so that the forehead support member 130 may be coupled to the rigid extensions 120.

The forehead support member 130, which is coupled to both rigid extensions 120, is preferably a flexible padded strap. Padding for the strap is preferably formed of a soft foam covered with a stain resistant material.

As shown in FIG. 2, the bottom outer portions 133 of the strap preferably include a hook and loop fastener strip 135 which may be used to fasten the forehead support member strap 130 to the rigid extensions 120. Since hook and loop fastener is used to couple the forehead support member 130 to the rigid extensions 120, it is readily understood that the forehead support member 130 is longitudinally adjustable along the length of the rigid extensions 120.

Figure 4:
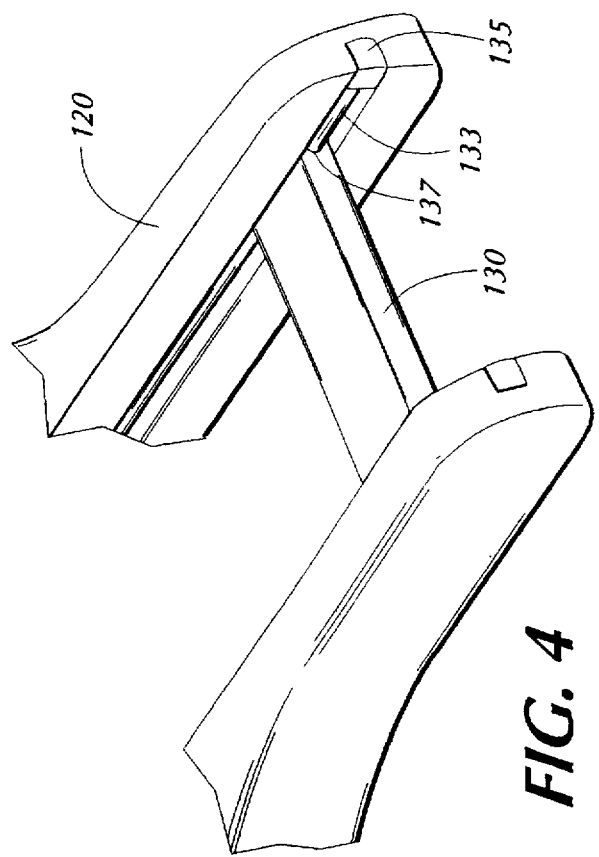
FIG. 4 is an isolated exploded perspective view of the face down body support apparatus of the present invention using rigid extensions having slide rods and the forehead support member having slots.

As shown in FIG. 4, the forehead support member 130 may also be a padded bar. The bar is preferably formed of a hard plastic, and the padding for the bar is preferably formed of a soft foam covered with a stain resistant material. For this embodiment, a slide rod 133 extends longitudinally along the inner length of the parallel portions of each rigid extension 120. Both outer portions 133 of the forehead support member 130 include a slot 137, which is mountable onto the slide rod 133 of the rigid extensions 120.

When the slots 137 of the forehead support member 130 are mounted onto the respective slide rods 133 of the rigid extensions 120, a locking mechanism 135 is used to lock the forehead support member 130 onto the slide rods 133 and to allow removal of the same. Since slide rods 133 are used to couple the forehead support member 130 to the rigid extensions 120, again it is readily understood that the forehead support member 130 is easily adjustable along the longitudinal axis of the rigid extensions 120.

Figure 5:
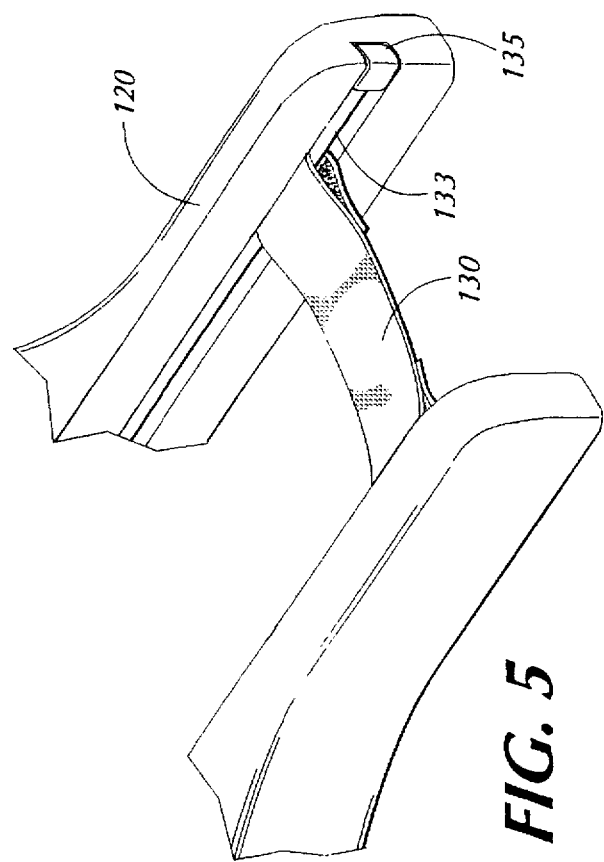
FIG. 5 is an isolated perspective view of the face down body support apparatus of the present invention using rigid extensions having slide rods and the forehead support member having hook and loop fastener.

Referring to FIG. 5, the forehead support member strap 130 of FIGS. 1 to 3 and the slide rods 133 of the rigid extension 120 of FIG. 4 may be used in tandem. As shown, the outer portions 133 of the forehead support member strap 130 are wrapped around the slide rods 133 to couple the forehead support member 130 to the rigid extensions 120. Again, since slide rods 133 are used, the forehead support member is easily adjusted along the length of the rigid extensions 120 and locked onto the slide rods 133 with the locking mechanism 135.

In use, the apparatus 100 is positioned on the upper end of a bed such that the rigid member 110 rests on the bed and the rigid extensions 120 are cantilevered from the head of the bed. A person then rests his or her abdomen on the contoured abdomen padding 112, chest on the contoured chest padding 114 and neck on the contoured neck padding 116. The person also suspends his or her arms along the tapered outer portions 123 of the rigid extensions 120. At this point, a majority of the person's body weight is distributed across the rigid member 110. Therefore, the person's body acts as the stabilizing means for keeping the apparatus 100 in place on the bed, and the apparatus 100 need not be fastened to the bed.

The person then rests his or her chin into the padded recessed member 140 and forehead onto the forehead support member 130. As described above, the forehead support member 130 is easily adjustably along the longitudinal axis of the rigid extensions 120. Therefore, the forehead support member 130 may be adjusted along the length of the rigid extensions for a comfortable and snug fit for the person's head.

Figure 6:
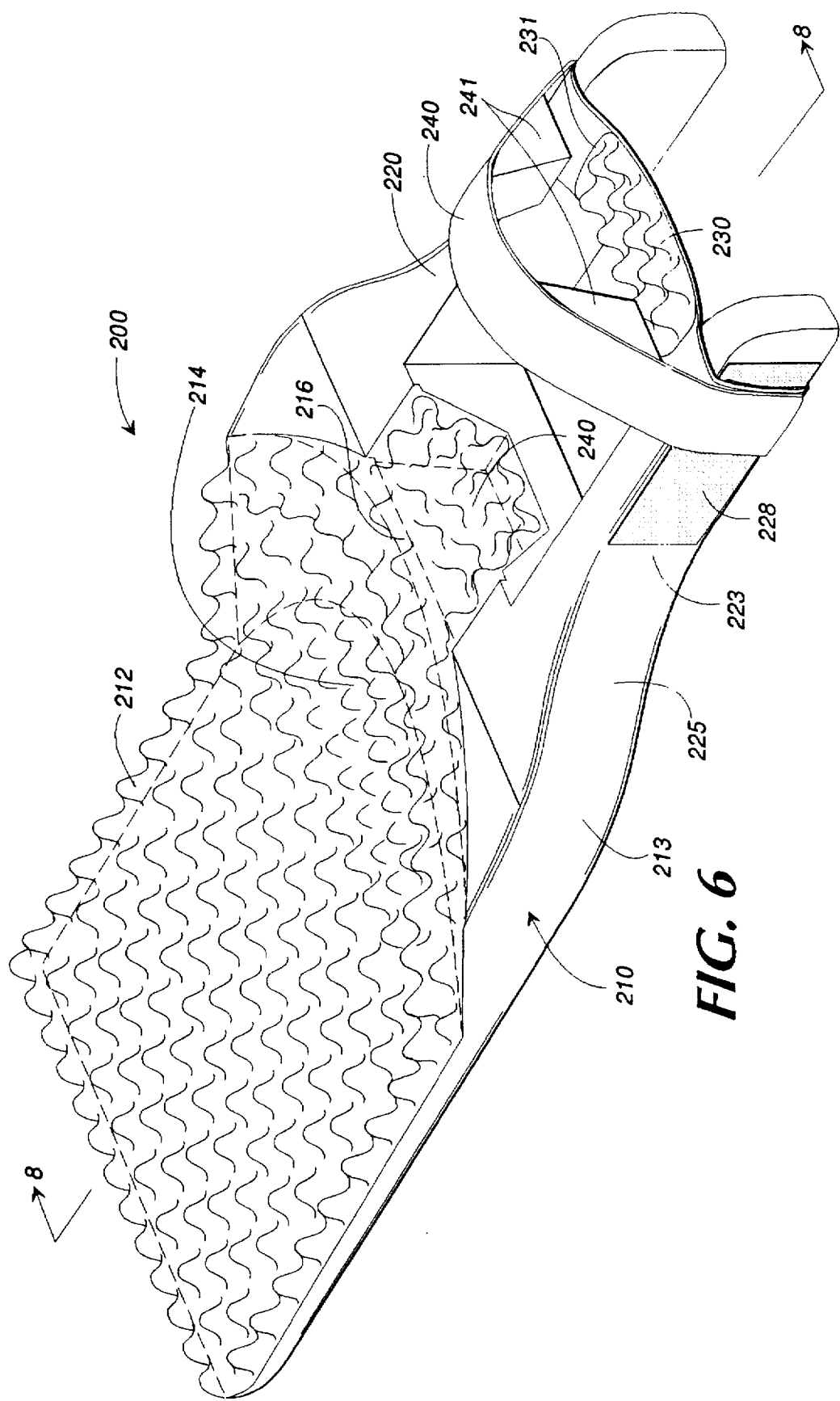
FIG. 6 is a perspective view of an alternative embodiment of the face down body support apparatus of the present invention using hook and loop fasteners on the rigid extensions and forehead support member.

FIG. 6 illustrates yet another embodiment of the present invention. In a manner similar to previous embodiments, the apparatus 200 includes a rigid member 210 for supporting a person's body, two rigid extensions 220 which extend outwardly from forward portion 213 of the rigid member 210 and a forehead support member 230 coupled to the two rigid extensions 220. The rigid member 210 may also be constructed of a biodegradable plastic material similar to that of rigid member 110.

The rigid member 210 preferably includes on its top surface a contoured abdomen padding 212, chest padding 214 and neck padding 216 to comfortably support these respective portions of a person's body. In this embodiment, the padding may comprise standard "egg-carton" contoured urethane foam, having components which allow the foam to be biodegradable, as previously explained.

A recessed member 240, which is preferably padded with the "egg-carton" contoured foam, extends downwardly from the upper portion 213 of the rigid member 210 to comfortably accept and support a person's chin.

The rigid member 210, including the recessed member 240, are preferably formed of a sufficiently stiff, lightweight, biodegradable plastic, as was explained above for member 110. Padding for the abdomen padding 212, chest padding 214 and neck padding 216 is preferably formed of an "egg carton" type of foam covered with a stain resistant material. As previously mentioned, all padding is preferably formed from a biodegradable polymer foam. Such a foam may be made from a urethane base, for example, with additives for allowing the foam to readily break down after the apparatus is discarded in a land fill. Further, the foam padding within recess 240 is preferably covered with a stain resistant material. Finally, all foam padding on rigid member 210 may include the "egg-carton" surface contour.

The outer portions 223 of the rigid extensions 220 preferably taper inward slightly as these extensions 220 extend away from the upper portion 213 of the rigid member 210 to approximately the mid-portion of each rigid extension 220. At the mid-portion, each rigid extension 220 substantially straightens out such that the outer portion 223 of the rigid extensions 220 are substantially parallel.

The tapered portion of the rigid extensions 220 provides an arm rest 225 for a person to comfortably support his or her arms. The outer portion 223 of each rigid extension 220 which is substantially parallel preferably includes a hook and loop fastener strip 228 extending substantially longitudinally along the length of the outer portion 223 so that the forehead support member 230 may be coupled to the rigid extensions 220.

The forehead support member 230, which is coupled to both rigid extensions 220, is preferably a flexible padded strap. Padding 231 for the strap is preferably formed of a soft foam having the "egg-carton" contour, and is preferably covered with a stain resistant material.

Bottom portions of the strap preferably include a hook and loop fastener strip in an inner portion thereof (not shown here but similar to the first embodiment) which may be used to fasten the forehead support member strap 230 to the rigid extensions 220. Since hook and loop fasteners are used to couple the forehead support member 230 to the rigid extensions 220, it is readily understood that the forehead support member 230 is longitudinally adjustable along the length of the rigid extensions 220.

Figure 7:
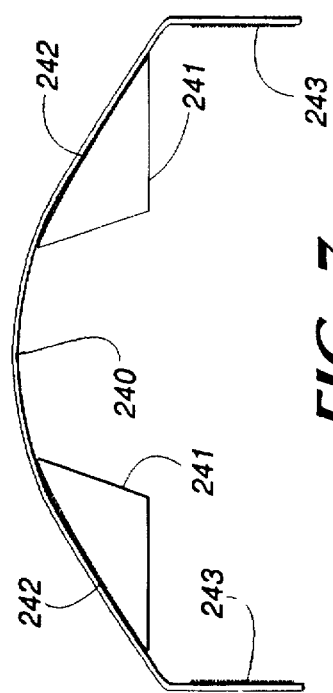
FIG. 7 is a front view of an overhead strap for use in combination with the present invention.

Apparatus 200 may also include an overhead strap 240. Strap 240 is adapted to engage a back side of a patient's head for securing and centering the person's head into the head support strap 230, and provides further stabilization for a patient who has a neck or back injury. As illustrated in FIG. 7, a bottom surface of strap 240 may include triangular pads 241 removably attached via hook and loop fastener strips. Pads 242 may be of the "egg-carton" contour type, and may be constructed of a biodegradable polymer as set forth above. Hook and loop fastener strips 243 may attach the over-head strap 240 directly to hook and loop fastener strips 238 on outer portions 223 on extensions 220. Alternatively, hook and loop fastener strips 243 may engage hook and loop fastener strips 244 on an outside surface of strap 230.

Figure 9:
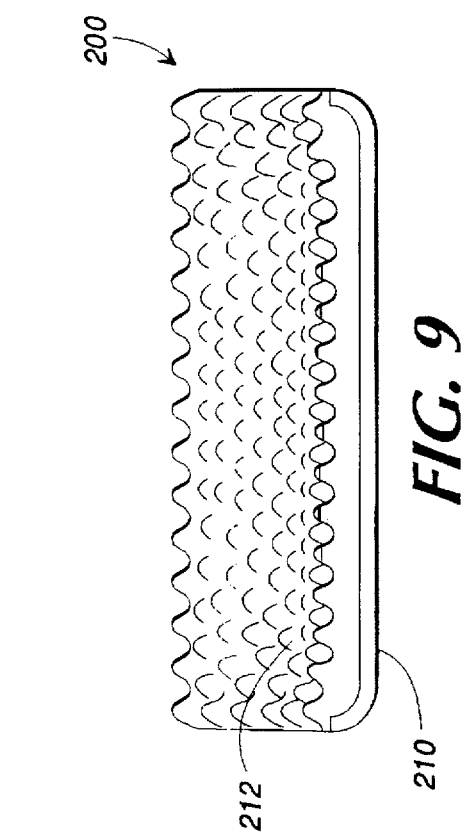
FIG. 9 is a rear view of the alternative embodiment of the face down body support apparatus of FIG. 6 illustrating the rigid member and its padding.
Figure 8:
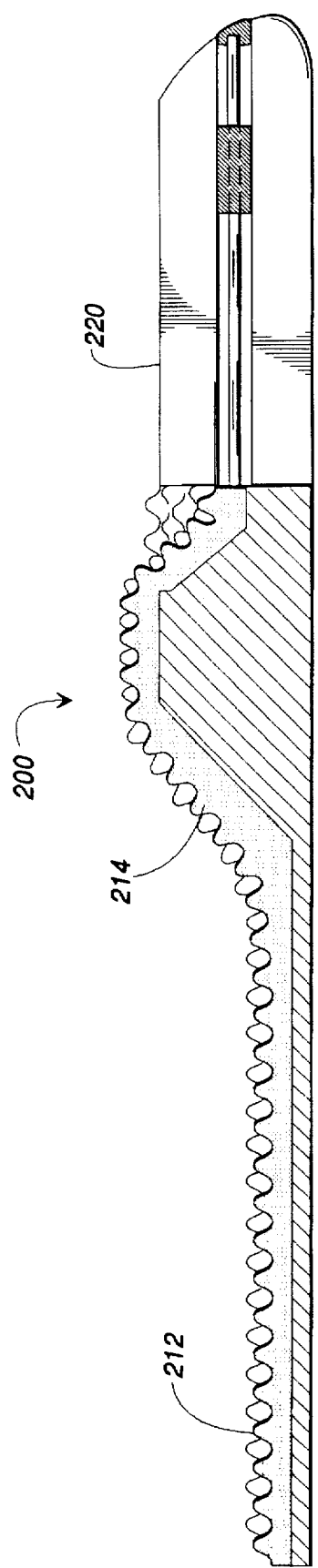
FIG. 8 is a cross-sectional view taken along line 8—8 of FIG. 6 of the alternative embodiment of the face down body support apparatus illustrating the rigid member and its padding.

FIG. 8 illustrates a cross-sectional view taken along line 8—8 of FIG. 6. As illustrated, in this embodiment rigid member 210 resembles a planar tray-like portion from its first end to the shoulder portion. Beginning at the shoulder and chest area, the rigid member gradually tapers upward toward the rigid extensions 220. Additionally, contoured abdomen padding 212 and contour chest padding 214 collectively taper upward from a first end of the rigid member 210 toward the extensions 220. FIG. 9 illustrates a rear view of the apparatus 200 illustrating the rigid member 210 at the left side of FIG. 8, which essentially resembles a plate-like structure having side portions which are tapered upward. Abdomen padding 212 fills the gaps between the upturned ends of the rigid member 210. Although the face-down apparatuses 200 and 100 may have any dimensions, the preferred dimensions are as follows: the width of the face down apparatuses 100 and 200 may be approximately 18 inches, a total length of the rigid member including its extensions may be approximately 35 inches, a maximum height of the extensions may be approximately 3½ inches, a length of the rigid extensions may be approximately 15 inches, a height of the rigid member at its first end may be approximately ¼ of an inch and a height of the padding at a first end of the face down apparatus may be approximately ¾ of an inch. Referring to FIG. 8 once again, it should also be noted near the shoulder and chest area of rigid member 210, a top surface of the rigid member 210 slopes upward near extensions 220 at a slope of approximately 35½ degrees as measured from a horizontal base, along a center line of the apparatus. Generally, the sloped portion is curved to conform with the person's chest, as is seen in FIG. 6. Additionally, it should be noted that the upturned ends of the rigid portion of the apparatus illustrated in FIG. 9 adds stiffness to the rigid member 210 for cantilevering of the patient's head off an end of the bed.

In use, the apparatus 200 is positioned on the upper end of a bed such that the rigid member 210 rests on the bed and the rigid extensions 220 are cantilevered from the head of the bed. A person then rests his or her abdomen on the contoured abdomen padding 212, chest on the contoured chest padding 214 and neck on the contoured neck padding 216. The person also suspends his or her arms along the tapered outer portions 223 of the rigid extensions 220. At this point, a majority of the person's body weight is distributed across the rigid member 210. Therefore, the person's body acts as the stabilizing means for keeping the apparatus 200 in place on the bed, and the apparatus 200 need not be fastened to the bed.

The person then rests his or her chin into the padded recessed member 240 and forehead onto the forehead support member 230. As described above, the forehead support member 230 is easily adjustably along the longitudinal axis of the rigid extensions 220. Therefore, the forehead support member 230 may be adjusted along the length of the rigid extensions for a comfortable and snug fit for the person's head. After the proper adjustments are made, strap 240 may then be secured over a back portion of the patient's head, using pads 241 to stabilize and center the patient's head. Strap 240 is secured to strip 228 or to strip 244, depending on the shape of a particular patient's head.

Once situated, the person can comfortably and securely lay face down for an extended period of time. Specifically, due to the contoured abdomen padding 212, chest padding 214, neck padding 216, tapered outer portions 223 of the rigid extensions 120 for the arms, padded recessed member 240 for the chin and forehead support member 230 for the forehead, the person may rest comfortably for a long period of time and need not be strapped into the face down position.

Further, by cantilevering the person's head over the head of the bed with the rigid extensions 220 and providing the opening between the recessed member 240 for the chin and the forehead support member 230, the person is provided with an opening which may serve several purposes. For instance, the opening provides an ample breathing passage for the person and provides sufficient space for the person to read, view a television and the like.

Another important aspect of the apparatus 200 of the present invention is that it is light weight and small making it easily portable. This is especially important in the medical field because medical personnel can easily move it from room to room, and patients can easily take the apparatus 200 home for further use.

It should be understood that various changes to the present invention may be made by the ordinarily skilled artisan without departing from the spirit and scope of the present invention which is presented in the following claims. The ordinary skilled artisan will readily understand that this disclosure presents an example of the invention and is not meant to limit the invention, as presented in the claims, in any way whatsoever.

I claim:

1. An apparatus for supporting a person face down, said apparatus comprising:
    a rigid member for supporting a person's body, said rigid member including
        first and second ends disposed opposite one another,
        a substantially planar bottom surface disposed between said first and second ends, wherein said bottom surface is adapted to engage a stable, horizontal surface, and
        a top surface having a contour near said second end which gradually increases in height with respect to said bottom surface as it approaches said second end forming a curved surface conforming substantially to that of a portion of a person's abdomen, chest and neck, wherein said top surface is adapted to engage and support a patient's abdomen, chest and neck;
    at least two rigid extensions extending outwardly from said second end of said rigid member in a substantially horizontal manner and substantially planar with respect to said planar bottom surface; and
    a forehead support member coupled to said at least two rigid extensions for supporting a person's forehead from beneath, when the person is lying in a face down position.

2. The apparatus of claim 1, wherein said top surface of said rigid body further defines a recessed member, said recessed member being disposed between said rigid extensions and having a bottom surface for supporting a person's chin.

3. The apparatus of claim 2, wherein said recessed member includes a padded surface.

4. The apparatus of claim 1, wherein said rigid member top surface includes a padded surface for supporting a portion of the person's body which contacts said rigid member top surface.

5. The apparatus of claim 1, wherein said rigid member is constructed from a biodegradable material.

6. The apparatus of claim 1, wherein said at least two rigid extensions extend substantially in parallel from said rigid member.

7. The apparatus of claim 1, wherein said forehead support member is coupled to said at least two extensions with hook and loop fasteners.

8. The apparatus of claim 1, wherein said forehead support member is longitudinally adjustable along the length of said at least two rigid extensions.

9. The apparatus of claim 1, wherein said forehead support member comprises a flexible strap.

10. The apparatus of claim 1, wherein said forehead support member comprises a rigid member.

11. The apparatus of claim 1, wherein said forehead support member includes a padding member for supporting the person's forehead.

12. The apparatus of claim 11, wherein in the padding is removably fastened to said forehead support member.

13. The apparatus of claim 12, wherein said removable padding is fastened to said forehead support member with hook and loop fasteners.

14. The apparatus of claim 12, wherein said removable padding is fastened to said forehead support member with hook and loop fasteners.

15. The apparatus of claim 1, further including an overhead member adapted to engage a rear portion of the patient's head for facilitating engagement of the person's head against said forehead support member.

16. The apparatus of claim 15, wherein said over-head support member comprises a flexible strap.

17. The apparatus of claim 16, wherein said overhead support member includes a padding member for securing the person's forehead.

18. The apparatus of claim 17, wherein in the padding is removably fastened to said forehead support member.

* * * * *